United States Patent [19]

Weeks

[11] Patent Number: Plant 5,855

[45] Date of Patent: Jan. 13, 1987

[54] ROSE PLANT NAMED INK SPOTS

[76] Inventor: O. L. Weeks, 926 W. Philadelphia, Ontario, Calif. 91761

[21] Appl. No.: 698,223

[22] Filed: Feb. 4, 1985

[51] Int. Cl.[4] ..... A01H 5/00

[52] U.S. Cl. ..... Plt./20

[58] Field of Search ..... Plt./20, 21

*Primary Examiner*—R. E. Bagwill

*Attorney, Agent, or Firm*—Vincent G. Gioia

[57] ABSTRACT

A new dark red hybrid tea rose variety with blackish markings on the petals.

1 Drawing Figure

The present invention relates to a new and distinct variety of rose plant of the hybrid tea rose class, which was originated by my crossing as seed and pollen parents two unnamed and unpatented seedlings of my creation. The denomination of this new rose is "Ink Spots".

Among the novel characteristics possessed by this new variety which distinguish it from its parents and all other varieties of which I am aware are its unusual and very dark red flowers with blackish markings, borne almost singly, one to a stem, on an outstanding plant with attractive foliage. Flowers are of good exhibition form and are desirable for cutting as well as garden decoration. The foliage is particularly outstanding which with fine plant growth habit and beautiful flowers result in a most satisfactory new cultivar. Asexual reproduction by budding of the new variety as performed in San Bernardino County, Calif., shows that the foregoing and other distinguishing characteristics come true to form and are established and transmitted through succeeding propagations.

The new variety differs from its parents in flower coloring, plant vigor and foliage. The seed parent is lighter red and the pollen parent is more orange red.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "187A" is plate 187A of The Royal Horticultural Society Colour Chart.

Parentage: Seedling.

*Seed parent.*—Unnamed seedling.

*Pollen parent.*—Unnamed seedling.

Class: Hybrid tea.

The following observations are made of specimens grown outdoors in San Bernardino County, Calif., during the month of October.

FLOWER

Blooming habit: Recurrent.

A. Bud:

(1) *Size.*—Medium to large.

(2) *Form.*—Short pointed.

(3) *Color.*—As sepals divide, buds are dark red with blackish coloring (near 187A) appearing primarily at the petal edges before they begin to unfurl.

(4) *Sepals.*—Longer than bud.

(5) *Peduncle.*—Length — medium. Aspect — upright, some small prickles. Strength — erect, strong. Color — near 144A, some with reddish overlay.

B. Bloom:

(1) *Size.*—Average size when fully expanded — about 3½ to 4 inches.

(2) *Borne.*—Singly, one to a stem.

(3) *Form.*—High centered, pointed bud opens with good high center remaining high, petals reflex and quill to points.

(4) *Petalage.*—Number of petals under normal conditions — about 25 to 28.

(5) *Color.*—As petals unfurl, flower coloring remains very dark red. Color approaches near to 45D but greyed with distinct blackish marking approaching near 187A in coloring. Flower coloring remains substantially the same from bud through open bloom stages. Blackish marking appears most commonly at petal edges or tips but also appears in veining on outer petals.

C. Petals:

(1) *Texture.*—Thick.

(2) *Appearance.*—Inside velvety and outside satiny.

(3) *Form.*—Ovate.

(4) *Arrangement.*—Regular.

(5) *Petaloids in center.*—Few, medium.

(6) *Persistence.*—Drop off cleanly.

(7) *Fragrance.*—Slight to none.

(8) *Lasting quality.*—Very long lasting quality on plant and as cut flower.

REPRODUCTIVE ORGANS

A. Stamens, filaments and anthers:

*Arrangement and color.*—Regularly arranged, pinkish red.

B. Pollen:

*Color.*—Golden yellow.

C. Styles: Uneven, medium.

D. Stigmas:

*Color.*—Creamy yellow.

E. Hips: None observed.

PLANT

A. Form: Upright, compact.

B. Growth: Vigorous.

*Height attained.*—About 4 to 5 feet.

C. Foliage: Compound 5 leaflets.

(1) *Size.*—Large.

(2) *Quantity.*—Abundant.

(3) *Color.*—New foliage: Upper side — reddish purple. Under side — reddish purple. Old foliage: Upper side — near 146A Under side — near to 147A.

(4) *Shape.*—Oval.

(5) *Texture.*—Upper side is waxy and veined and under side is dull and veined.

(6) *Edge.*—Serrate.

(7) *Serration.*—Ordinary.

(8) *Leaf stem.*—Color — near to 147B to A. Under side — near 147C.

(9) *Stipules.*—Medium and slightly bearded.

(10) *Resistance to disease.*—Average.

D. Wood:

(1) *New wood.*—Color—pale green with reddish overlay. Bark — smooth.

(2) *Old wood.*—Color — near 147B. Bark — smooth.

E. Thorns:

(1) *Thorns.*—Quantity (main stalk) — very few. On laterals from stalk — very few. Form — flat. Length — small. Color — tan. Position — irregular.

(2) *Prickles.*—Few to none.

F. Winter hardiness: Needs winter protection in severe climate.

I claim:

1. A new and distinct variety of rose plant of the hybrid tea rose class, substantially as shown and described, characterized particularly by well formed, very dark red flowers with blackish markings on the petals borne one to a stem on a vigorous plant with attractive foliage and which are long lasting on the plant and as cut flowers.

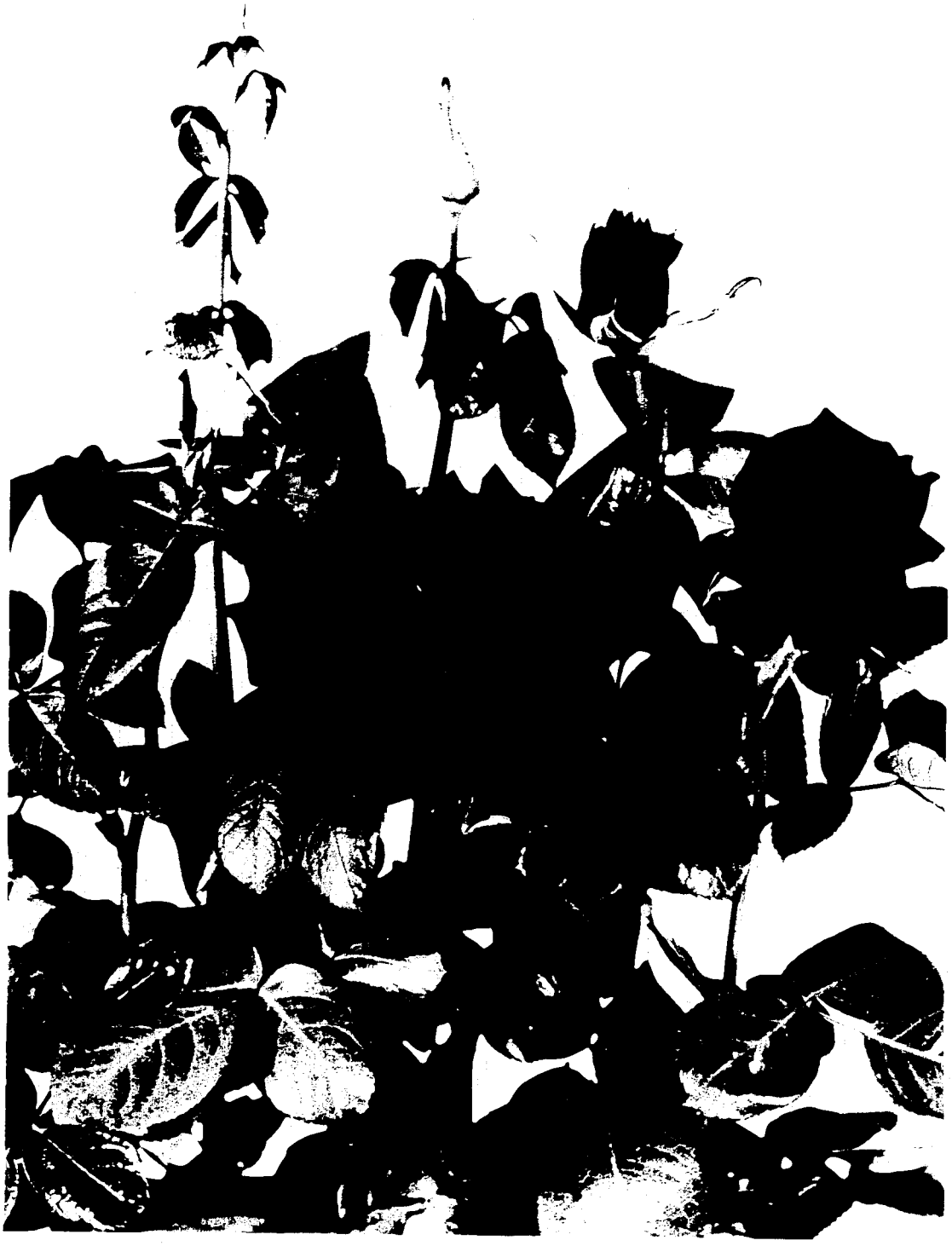

* * * * *